United States Patent

Yatsugake et al.

[11] Patent Number: 5,903,342
[45] Date of Patent: *May 11, 1999

[54] INSPECTION METHOD AND DEVICE OF WAFER SURFACE

[75] Inventors: Yasuo Yatsugake, Saitama-ken; Takashi Okawa, Fujioka; Norihiko Mizutani, Saitama-ken; Shigeharu Iizuka, Honjo, all of Japan

[73] Assignee: Hitachi Electronics Engineering, Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/629,266

[22] Filed: Apr. 8, 1996

[30] Foreign Application Priority Data

Apr. 10, 1995 [JP] Japan ................................ 7-108961
Jan. 30, 1996 [JP] Japan ................................ 8-35480

[51] Int. Cl.$^6$ .................................................. G01N 21/88
[52] U.S. Cl. ................................... 356/237.4; 356/237.5; 356/239.8; 250/559.41
[58] Field of Search .................................. 356/237, 239, 356/338, 394, 364–369, 445–446, 237.1, 237.2, 237.4, 237.5, 239.1, 239.3, 239.7, 239.8; 250/225, 572, 578, 562, 563, 559.41

[56] References Cited

U.S. PATENT DOCUMENTS

| | | | |
|---|---|---|---|
| 4,610,541 | 9/1986 | Tanimoto et al. | 356/237 |
| 4,889,998 | 12/1989 | Hayano et al. | 356/237 |
| 4,966,457 | 10/1990 | Hayano et al. | 356/237 |
| 5,245,403 | 9/1993 | Kato et al. | 356/327 |
| 5,293,538 | 3/1994 | Iwata et al. | 356/237 |

FOREIGN PATENT DOCUMENTS

| | | | |
|---|---|---|---|
| 0207953 | 9/1986 | Japan | 356/237 |
| 0143831 | 6/1988 | Japan | 356/237 |
| 0088237 | 4/1989 | Japan | 356/237 |

*Primary Examiner*—Hoa Q. Pham
*Attorney, Agent, or Firm*—Fay, Sharpe, Beall, Fagan, Minnich & McKee

[57] ABSTRACT

A wafer surface inspection method and device including a low angle light receiving system having an elevation angle less than 30° with reference to the wafer surface, and a high angle light receiving system having an elevation angle equal to or larger than 30°, scans the wafer with a laser beam, receives scattered light to perform extraneous substance detection in response to the scanning, and detects wafer defects only by the high angle light receiving system, and sticking extraneous substances by either the low angle receiving system or by both the low angle light receiving system and the high angle light receiving system.

16 Claims, 10 Drawing Sheets

INSPECTION METHOD AND DEVICE OF WAFER SURFACE

BACKGROUND OF THE INVENTION

1. Field of the Invention

The present invention relates to a method and device for inspecting a wafer surface and, more specifically, relates to an inspection method and device which distinguishes between extraneous substances sticking on a surface of a silicon wafer and crystal defects existing on the surface thereof.

2. Background Art

A silicon wafer base material for semiconductor ICs is manufactured from a highly purified polycrystalline silicon. Namely, the silicon wafer is manufactured in the following manners in that at first an ingot of a moncrystalline silicon is prepared via a pull-up method, for example the prepared ingot is sliced into thin plates, the surface of the sliced thin plate is polished to a mirror surface, and thereafter extraneous substances sticking on the surface thereof are carefully cleaned off. In spite of such careful cleaning, some sticking extraneous substances may remain on the surface thereof. If many sticking extraneous substances remain on the wafer surface, the quality of ICs produced from the silicon wafer is degraded. For this reason, the surface of the silicon wafer is inspected for remaining sticking extraneous substances and the degree thereof via a surface inspection device.

Figure 10A:
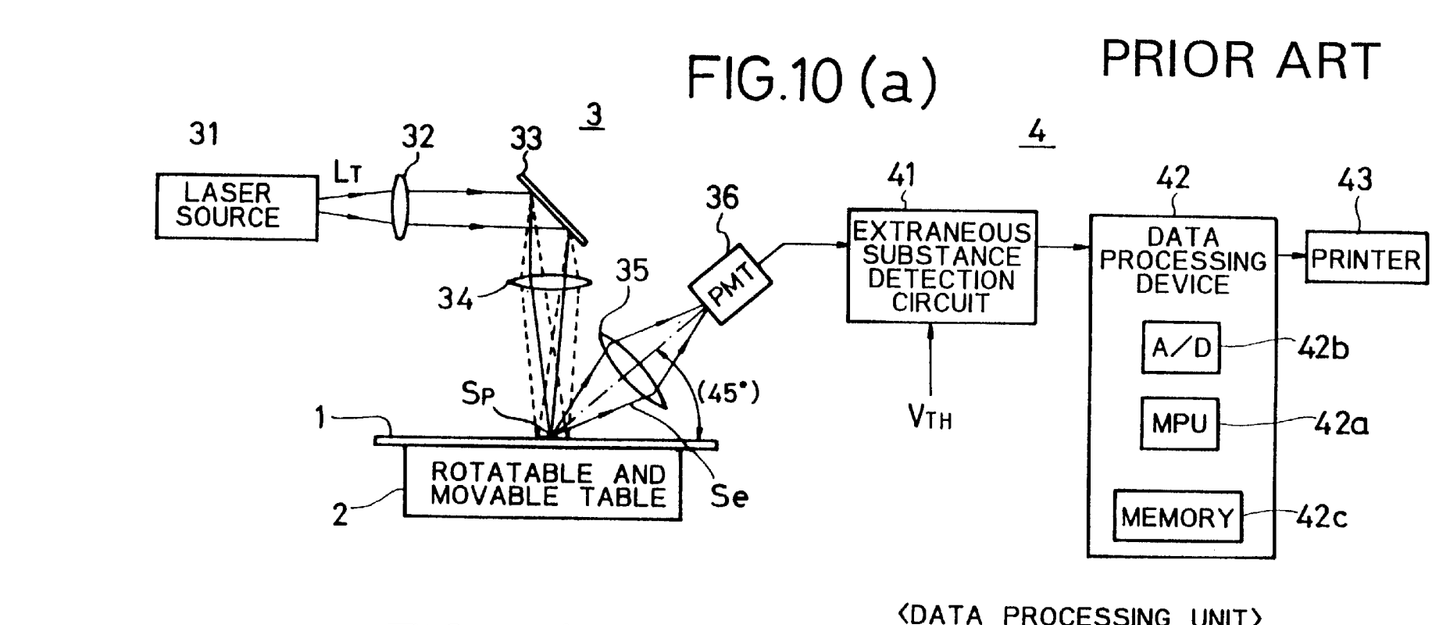

FIG. 10(a) shows a constitution of a conventional wafer surface inspection device. As illustrated in FIG. 10(a), the surface inspection device is constituted by, for example a rotatable and movable table 2, an inspection optical system 3 and a data processing unit 4. A silicon wafer (hereinbelow simply called a wafer) 1, which is an object for the inspection, is placed on the rotatable and movable table 2. The inspection optical system arranged above the wafer 1 includes a laser source 31 provided with a laser oscillating tube. The laser beam LT outputted from the laser source 31 is made parallel via a collimator lens 32 and is scanned in the X direction by a vibrating mirror 33. Then, the scanned laser beam is focused by a focusing lens 34 as a laser spot Sp (hereinbelow simply called a spot Sp) and is projected perpendicularly onto the surface of the wafer 1 to scan the wafer in response to the movement of the wafer 1.

The wafer 1 is rotated by the rotatable and movable table 2 as well as moved in the radial direction (X direction). Thereby, the spot Sp scans the surface of the wafer 1 in a spiral manner so that the entire surface of the wafer 1 is scanned. The driving of the rotatable and movable table 2 is controlled via the data processing unit 4 which is explained later.

Figure 10B:
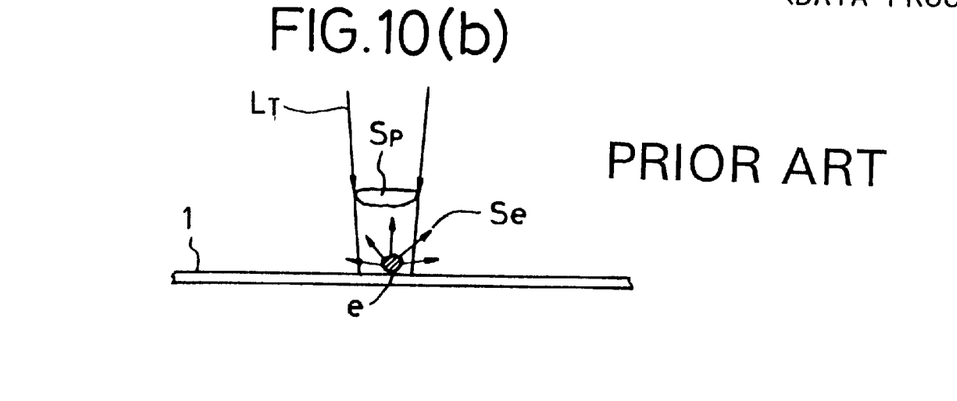

When an extraneous substance e exists on the surface of the wafer 1 as illustrated in FIG. 10(b), the spot Sp induces scattering light Se in random directions due to the extraneous substance e. A part of the scattering light Se is condensed by a condensing lens 35, the optical axis of which forms a 45° angle with respect to the wafer surface, and is received by a photomultiplier tube (PMT) 36 serving as a photoelectric converter. The incident light into the PMT 36 is converted herein into an electrical signal and the converted received light signal is inputted into an extraneous substance detection circuit 41.

The extraneous substance detection circuit 41 compares the received light signal with a predetermined threshold value $V_{TH}$ via a differential amplifier of one side amplification, and amplifies the component exceeding the threshold value $V_{TH}$. Thereby, a detection signal (analog signal) of which the noise component is removed is input into the data processing unit 4.

The detection signal is converted into a digital value via an A/D converter circuit (A/D) 42b provided in a data processing device 42 and is stored once in a memory 42c via an MPU 42a when the MPU 42a executes a predetermined programs the detection data is processed together with the data of the concerned scanning position (detection position). As a result, the size of the extraneous substance e is judged depending on the detection values Further, the number of the extraneous substances is counted. Still furthers through execution of a predetermined program via the MPU 42a, data of extraneous substances representing the size, number and position of the extraneous substances e are produced and outputted such as to a printer 43 and a display (not shown) to display the conditions of the extraneous substances in a map form. Still furthers the A/D 42b can be provided outside the data processing device 42.

The above mentioned spot Sp has a diameter of about a few $\mu$m and is a very intense light, and a condenser lens having a large diameter and a wide condensing angle is used for the condenser lens 35. Furthers the PMT 36 has a large amplification rate and a low noise characteristic. Thereby, even an extraneous substance or a defect having a diameter of about 0.1 $\mu$m can be detected.

Further, the scanning by the spot Sp for the wafer 1 can be performed by XY scanning instead of the rotating scanning method.

In connection with a recent improvement of the integration density of ICs and related miniaturization of their wirings, the limit of allowable size of extraneous substances to be detected is further lowered. For this reason, even a defect due to loss of atoms in the silicon atom lattice of the wafer 1 is considered to be a problem which is explained with reference to FIGS. 11 and 12.

Figure 11:
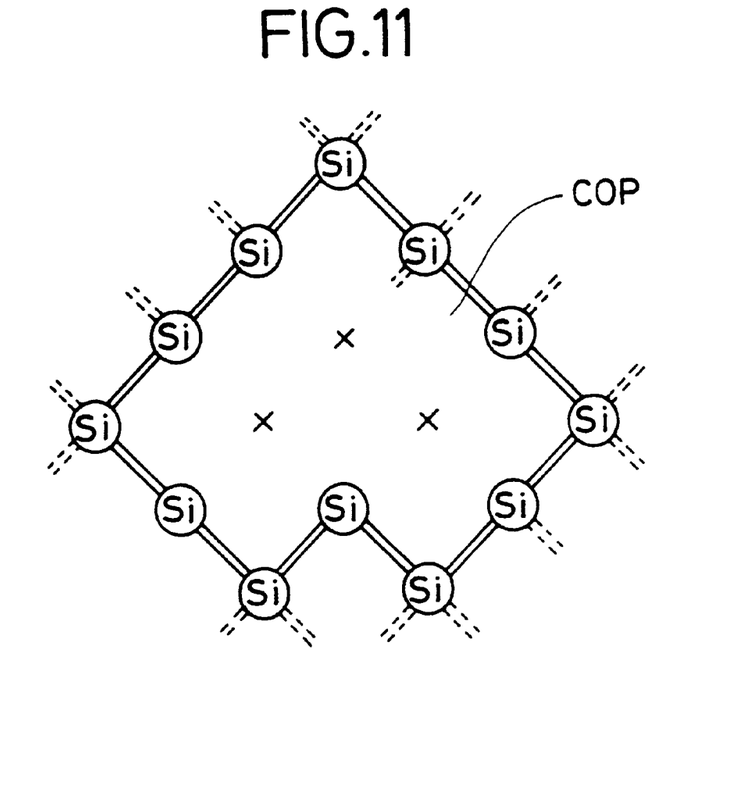
FIG. 11 is a view for explaining a crystal defect (COP)

The wafer is constituted by a single crystal in which a multiplicity of silicon atoms Si are mutually connected in a lattice form. As illustrated in FIG. 11, when silicon atoms Si are oxidized and microscopic oxides thereof are formed on the surface thereof, and if the microscopic oxides are removed by cleaning, a loss of atoms can be induced which causes a crystal defect. Such a crystal defect is called a Crystal Originated Particle (COP), which term is used hereinbelow.

Figure 12:
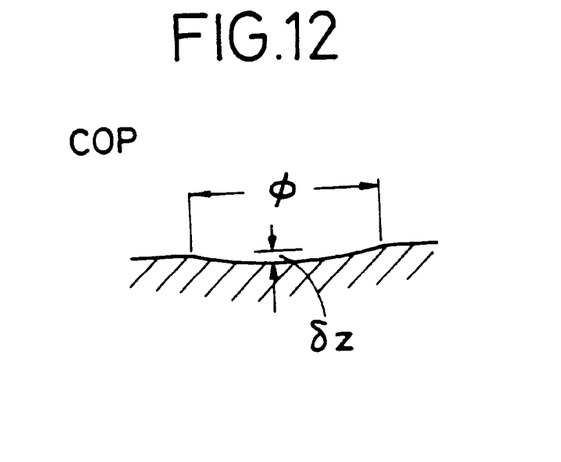
FIG. 12 is a view for explaining the configuration of a COP.

In FIG. 11, a plurality of contigous silicon atoms Si (in the drawing three) are lost. When observing the portion of the water loss via a microscopes the cross section thereof is recessed as illustrated in FIG. 12. Although a variety of diameters $\phi$ and the depths $\delta z$ of such recesses can be observed, such recesses show a common characteristic that the depth $\delta z$ is comparatively small in comparison with the diameter $\phi$ thereof. For example, where a diameter $\phi$ is 1~2 $\mu$m, the depth $\delta z$ thereof is about 0.05~0.1 $\mu$m which is about one twentieth of the diameter. The size of a COP defect varies depending on ICs, in that a COP having diameter $\phi$ of 2 $\mu$m is no problem for an IC memory of 16M bits, but is a problem for an IC memory of more than 64M bits.

The number of COPs varies depending on the pull-up speed when manufacturing an ingot of a single crystal silicon and number of cleanings of the wafer. On the other hand, the number of sticking extraneous substances decreases depending on the number of cleanings. Therefore, the pull-up speed and the number of cleanings have to be determined properly. For this reasons it becomes necessary to separately measure the number and size of COPs and sticking extraneous substances.

Therefore, it is demanded to measure the COPs with a wafer surface inspection device and to obtain an evaluation data thereof. However, with the above explained detection optical system 3, sticking extraneous substances as well as COPs are detected at the same time such that separate measurement of the number of both or the number and size of both has not been possible.

With regard to the extraneous substance inspection device, U.S. Pat. No. 5,245,403 entitled "APPARATUS FOR DETECTING EXTRANEOUS SUBSTANCES ON A GLASS PLATE" of the same assignee as the present application discloses two light projecting systems of high and low angles.

SUMMARY OF THE INVENTION

An object of the present invention is to provide a wafer surface inspection method which permits detection of both sticking extraneous substances and COPs.

Another object of the present invention is to provide a wafer surface inspection device which permits detection of both sticking extraneous substances and COPs.

Features of the wafer surface inspection method and device according to the present invention which achieve the above objects include a low angle light receiving system having an elevation angle less than 30° with reference to the wafer surface, and a high angle light receiving system having a elevation angle equal to or larger than 30°, wherein the wafer is scanned by a laser beam, the low angle light receiving system and the high angle light receiving system are adapted to receive scattered light of the laser beam to perform extraneous substance detection in response to the scanning, and matter detected only by the high angle light receiving system at a particular scanning position is determined as a defect of the wafer, while matter detected only by the low angle light receiving system or by both the low angle light receiving system and the high angle light receiving system at the scanning position is determined as a sticking extraneous substance.

Further, if required, the size of the extraneous substances and the defects is judged depending on the detection value thereof determined by the high angle light receiving system.

The inspection device according to the present invention includes a first photo electric converter provided in the low angle light receiving system a second photo electric converter provided in the high angle light receiving system, and a data processing device which receives a first detection signal from the first photo electric converter and a second detection signal from the second photo electric converter and determines a detected matter as a sticking extraneous substance when only the first detection signal exceeds a predetermined value, or when both the first detection signal and the second detection signal exceed respective predetermined values, and further determines a detected matter as a defect when only the second detection signal exceeds the predetermined value.

Now, an experimental study performed by the present inventors with regard to directivity of scattered light from sticking extraneous substances and crystal defects is explained. The directivity of the scattered light from the sticking extraneous substance is nondirectional, however, because the depth of a normal crystal defect is very shallow in comparison with the diameter thereof, the scattering light from the crystal defect shows a directivity more than 30° with respect to the wafer surface and substantially no scattering light can be observed in the direction below 30°.

Because of the above explained directivity, scattering light received from both the sticking extraneous substance and the crystal defect is received by the high angle light receiving system provided at an elevation angle of 35°~60° with respect to the reference wafer surface, to thereby detect both the sticking extraneous substance and the crystal defect. On the other hand, in the low angle light receiving system provided at an elevation angle of less than 30°, substantially no scattering light from a crystal defect is received, but only the scattering light from an extraneous substance is received, to thereby detect the sticking extraneous substance.

As will be presumed from the above explanation of the conventional art, a light receiving system at an elevation angle of about 35°~60° can receive an intense scattering light from possible crystal defects, sticking extraneous substances and the likes In particular, an optimum range for receiving such intense scattering light is 40°~50°.

Figure 7A:
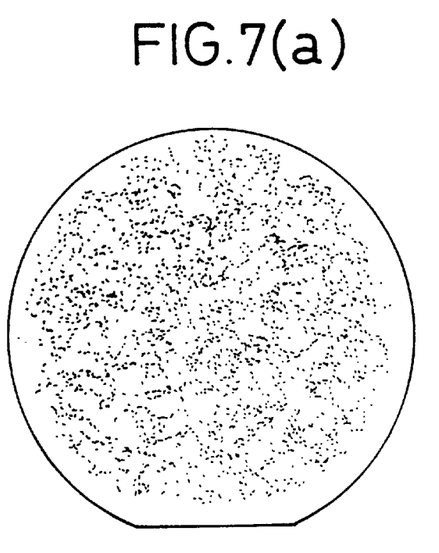
Figure 7B:
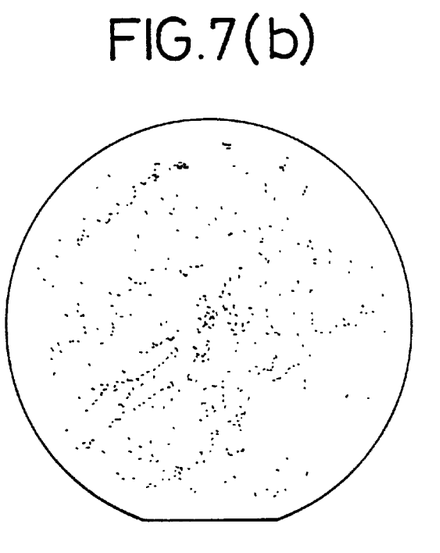
FIG. 7(b) shows another map of extraneous substance detection data on the same wafer as in FIG. 7(a) when scattering light is received at a low elevation angle of 5°~20°, further

The scattering light reception with the low angle light receiving system having an elevation angle of less than 30° is based on the experimental result as illustrated in FIGS. 7(a) through 7(d). Namely, FIG. 7(a) shows an example of maps of extraneous substance detection data on a wafer manufactured through the CZOCHRALSKI method while receiving the scattering light at a high angle having an elevation angle of 40°~50°, and FIG. 7(b) shows an example of maps of extraneous substance detection data on the same wafer when receiving the scattering light at a low angle having an elevation angle of 5°~20°. As will be apparent from the comparison of these maps, FIG. 7(a) shows a large number of detections which contains both sticking extraneous substances and crystal defects. On the other hand, FIG. 7(b) shows a small number of detections which only contains detection of sticking extraneous substances.

Figure 7C:
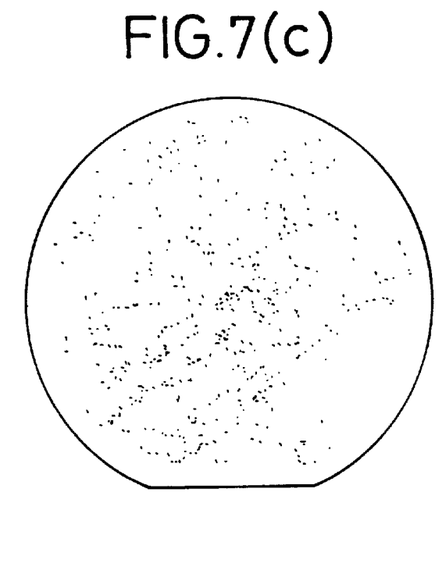
FIG. 7(c) shows a map of extraneous substance detection data of a wafer manufactured by the FLOATING ZONE method when scattering light is received at a high elevation angle of 40°~50°.
Figure 7D:
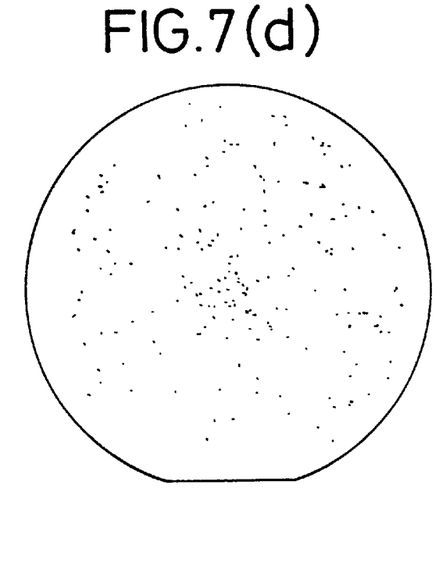
FIG. 7(d) shows another map of extraneous substance detection data on the same wafer as in FIG. 7(c) when scattering light is received at a lower elevation angle of 5°~20°.

Since it is quite difficult to inspect a wafer from which sticking extraneous substances are completely removed, in order to prove the above difference an extraneous substance detection is performed on a wafer manufactured via the FLOATING ZONE method through which COP defects are rarely induced. FIG. 7(c) shows the detection data when the scattering light is received at a high elevation angle of 40°~50° and FIG. 7(d) shows the detection data when received at a low elevation angle of 5°~20°. Unlike the previous maps shown in FIGS. FIGS. 7(a) and 7(b), the map shown in FIG. 7(c) is substantially the same as the map shown in FIG. 7(d).

These maps are typical examples of the detection and when the above indicated angle ranges are shifted somewhat upwardly and downwardly no substantial difference occurs. However, when the optical axis of the low angle light receiving system exceeds 30°, the condition illustrated in FIG. 7(b) comes close to the condition illustrated in FIG. 7(a).

Figure 8:
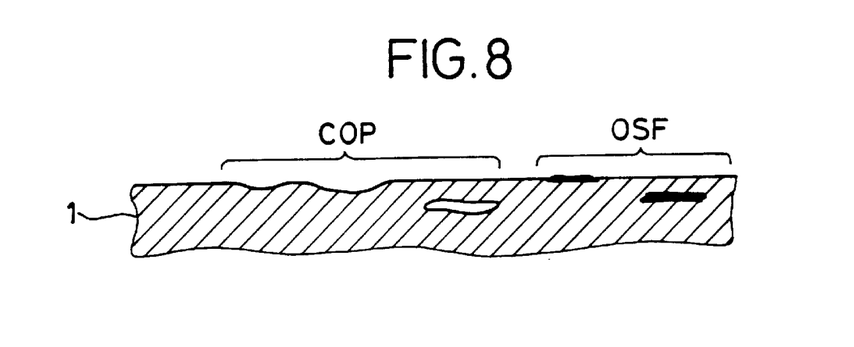
FIG. 8 is a view for explaining crystal defects (COP) and oxidation induced stacking faults (OSF) which occur on the surface and inside the wafer.

It has been recognized recently that the COPs occur even inside the wafer as illustrated in FIG. 8. In addition, on the surface of the wafer an Oxidation induced Stacking Fault (OSF) further occurs. When a light spot is irradiated on these two as explained above, the scattering light is induced therefrom like the sticking extraneous substances, and the scattering light from these two operates as noise when the amplification rate of the PMT is increased. Such noise causes a problem when detecting sticking extraneous substances with the low angle light receiving system having a comparatively low detection level.

Accordingly, the present inventors noticed a Brewster angle $\theta_B$ at which the reflection rate of the P-polarized light component is substantially zero. By making use of the Brewster angle $\theta_B$ for the low angle light receiving system the noise component induced by the scattering light from the COPs and OSFs is reduced and a more accurated detection of sticking extraneous substances is realized.

The Brewster angle $\theta_B$ of the wafer 1 can be calculated based on the refraction factor n of silicon. However, the refraction factors n of such materials as silicon and glass generally vary depending on wave length $\lambda$. For example, the refraction factor n of silicon for an optical wave having a wave length of 3 $\mu$m is indicated as 3.43 in an optical handbook and the like. However, this value cannot be used as it is for a detection optical system.

Figure 9:
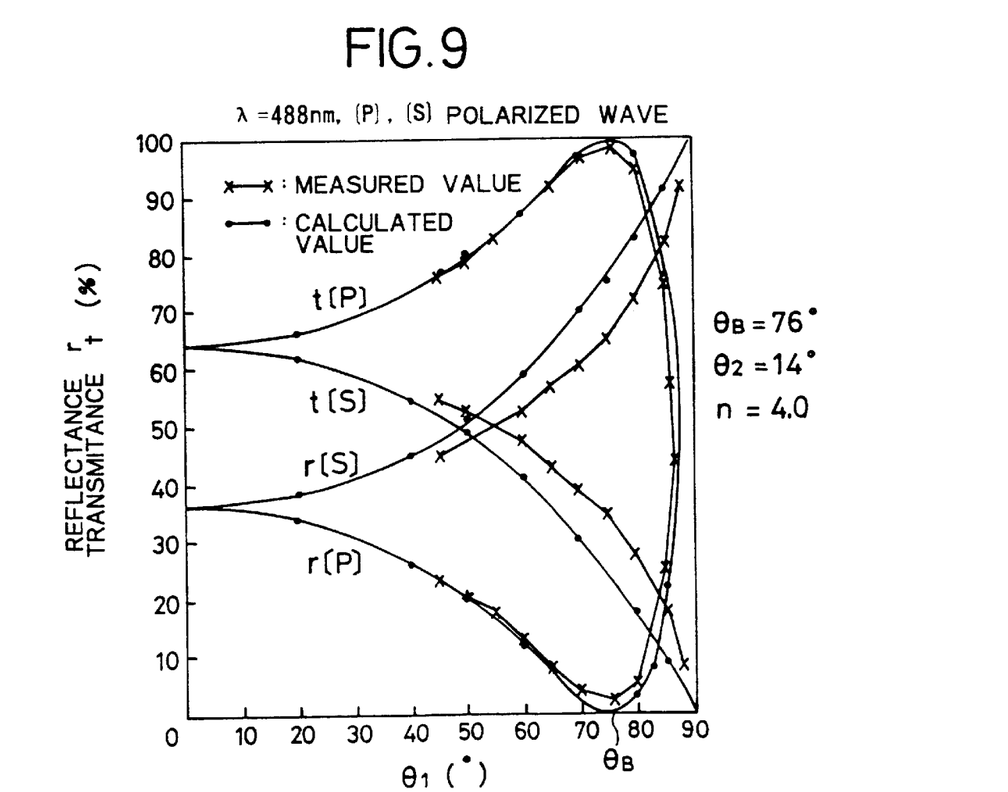
FIG. 9 is a graph illustrating a relationship between experimental data and theoretical value at the Brewster angle.

FIG. 9 graphs experimental data with respect to Brewster angle, the abscissa representing the incidence angle $\theta 1$ and the ordinate representing the reflection rate r and the transmittance t in %. An argon laser tube is used as a laser source, P-and S-polarized waves are prepared by changing the linear polarized wave having a wave length of 488 nm which is generated through oscillation of the laser source, the respective polarized waves are projected onto the surface of the wafer 1, and the reflection rate r[p] (wherein [p] denotes the P-polarized component), transmittance t[p], reflection rate r[S] (wherein [S] denotes the S-polarized component) and transmittance t[S] for the incident angle $\theta 1$ are respectively measured. As a result, actual measured values indicated by crosses X are obtained. Since the reflection rate r[p] is minimized at an incidence angle of 76°, the angle is provisionally assumed as the Brewster angle $\theta_B$. Accordingly, when assuming the refraction angle as $\theta_2$, the $\theta_2$ is given as 14° which falls within the above determined range of 5°~20°.

Now, when light flux having P-polarized waves and S-polarized waves is projected from air having a refraction factor n1=1 onto the surface of a dielectric body having a refraction factor n2 with a proper incidence angle of $\theta 1$, the relationship of $n1 \sin\theta 1 = n2 \sin\theta 2$ stands. When substituting $\theta 1=76°$ and $\theta 2=14°$ into the above theoretical equation to determine n2, an actual refraction factor n2=4.0 is obtained for the silicon wafer.

Based on the above obtained result, theoretical values of r[P], t[P] r[S] and t[S] are calculated which are illustrated by solid dots.

Although the actual measured values of r[P] and t[P] deviate by about 1% from the theoretical values near the Brewster angle $\theta_B(76°)$, the actual measured values thereof other than the above substantially agree with the calculated values. However, the actual measured values of r[S] and t[S] do not agree with the calculated values.

According to the above experimental result, the angle of the low angle light receiving system is determined at about 14° and further a light projecting system having an irradiation angle equal to the above angle and including a light source of P-polarized light is provided. The low angle light receiving system is provided with an S-polarization filter through which the scattering light is received. With this measure, only the sticking extraneous substances are further correctly detected.

When a sticking extraneous substance receives the light of the P-polarized wave and scatters the same, scattering light containing a P-polarized component and an S-polarized component is generated; however, the reflection light from the surface of the COP and OSF primarily contains only P-polarized component. Thus these P-polarized components are cut by the S-polarized filter to detect the sticking extraneous substance. Thereby, the reception of the scattering light from the COP and the OSF is eliminated, the S/N ratio is improved, and, in particular, a correct detection of sticking extraneous substances is realized while suppressing the influence of noise by slightly reducing the sensitivity (amplification rate) of the PMT.

BRIEF DESCRIPTION OF THE DRAWINGS

FIG. 7(a), 7(b), 7(c) and 7(d) are views for explaining a directivity characteristic of the scattering light from a sticking extraneous substance and from a COP according to the present invention, wherein FIG. 7(a) shows a map of extraneous substance detection data on a wafer manufactured by the CZOCHRALSKI method when scattering light is received at a high angle having an elevation angle of 40°~50°.

FIGS. 10(a) and 10(b) show a conventional wafer surface inspection device, wherein FIG. 10(a) shows a constitutional diagram thereof and FIG. 10(b) is a view for explaining light scattering conditions when light is irradiated onto an extraneous substance;

DETAILED DESCRIPTION OF PREFERRED EMBODIMENTS

Figure 1:
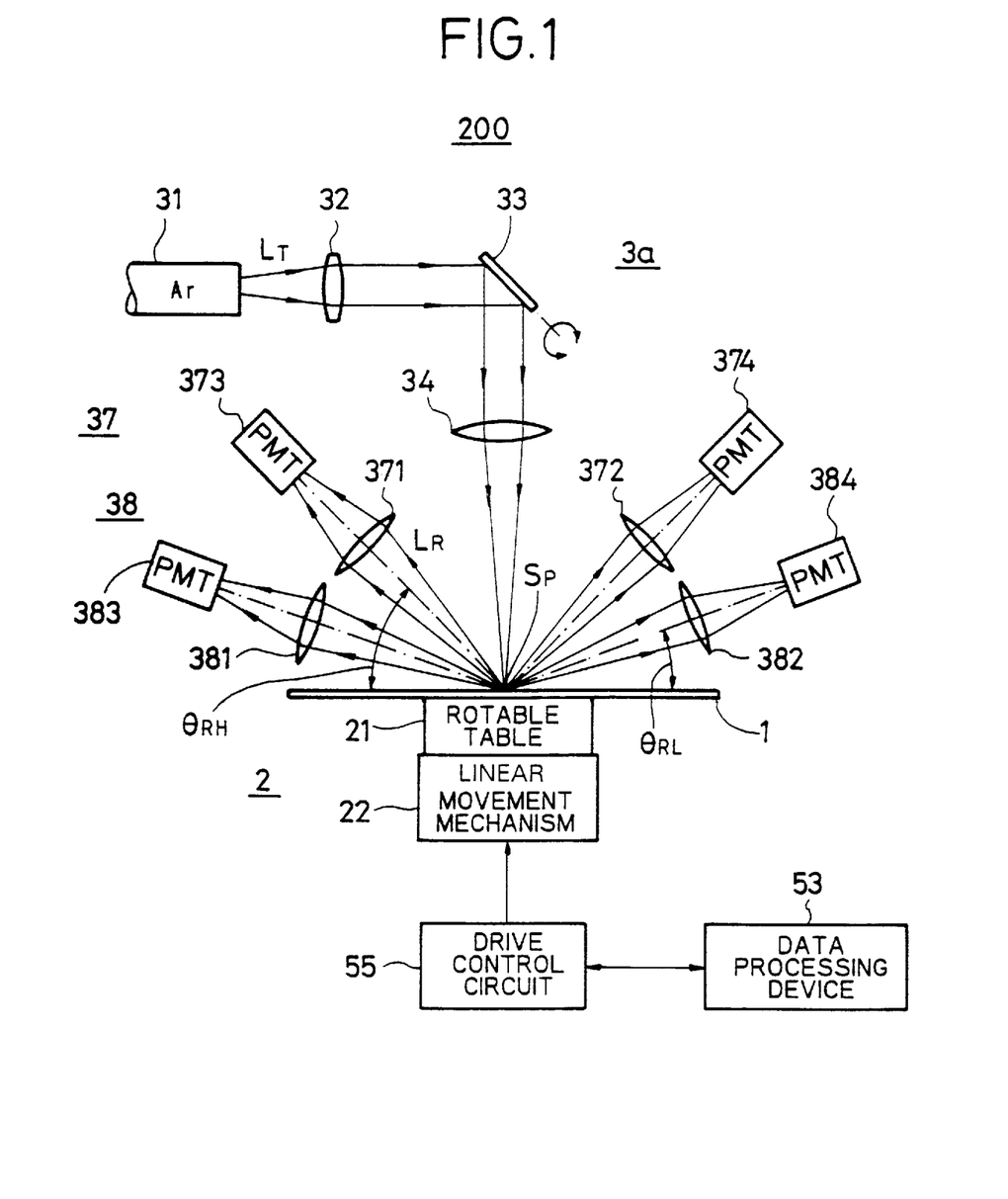
FIG. 1 is a view for explaining a detection optical system in a wafer surface inspection device according to the present invention.

FIG. 1 shows an optical inspection system according to the present invention in which the same elements as in FIG. 10 are designated by the same reference numerals as in FIG. 10.

An optical inspection system 3a in a wafer surface inspection device 200 as illustrated in FIG. 1 has substantially the same constitution as the optical inspection system 3 as explained in connection with FIG. 10; however, different from the device in FIG. 10 in the optical inspection system 3a, two high and low angle light receiving systems respectively disposed at right and left sides are provided. The first light receiving system is a high angle light receiving system 37 having an elevation angle of 40°~50° with reference to the surface of the wafer 1, and the second light receiving system is a low angle light receiving system 38 having an elevation angle of 5°~20°.

The rotatable and movable table 2 is constituted by a rotatable table 21 and linear movement mechanism 22 which linearly moves the rotatable table 21, and the position and rotation of the rotatable and movable table 2 is controlled via a drive control circuit 55 by a data processing device 53 which will be explained later.

A laser scanning system using rotating scanning method like that shown in FIG. 10 is used. however, the system can be replaced by a system using XY scanning.

The high angle light receiving system 37 is constituted by a first set including of a focusing lens 371 and a PMT 373, and by a second set including a focusing lens 372 and a PMT 374 disposed symmetrically at the left and right sides, respectively. The elevation angle $\theta_{RH}$ of the optical axis of the high angle light receiving system 37 with reference to the surface of the wafer I is set in a range of 40°~50°. The low angle light receiving system 38 is similarly constituted by a first set including a of focusing lens 381 and a PMT 383, and by a second set including a focusing lens 382 and a PMT 384, disposed symmetrically at the left and right sides, respectively. The elevation angle $\theta_{RL}$ of the optical axis of the low angle light receiving system 38 with reference to the surface of the wafer 1 is set in a range of 5°~20°.

Figure 2:
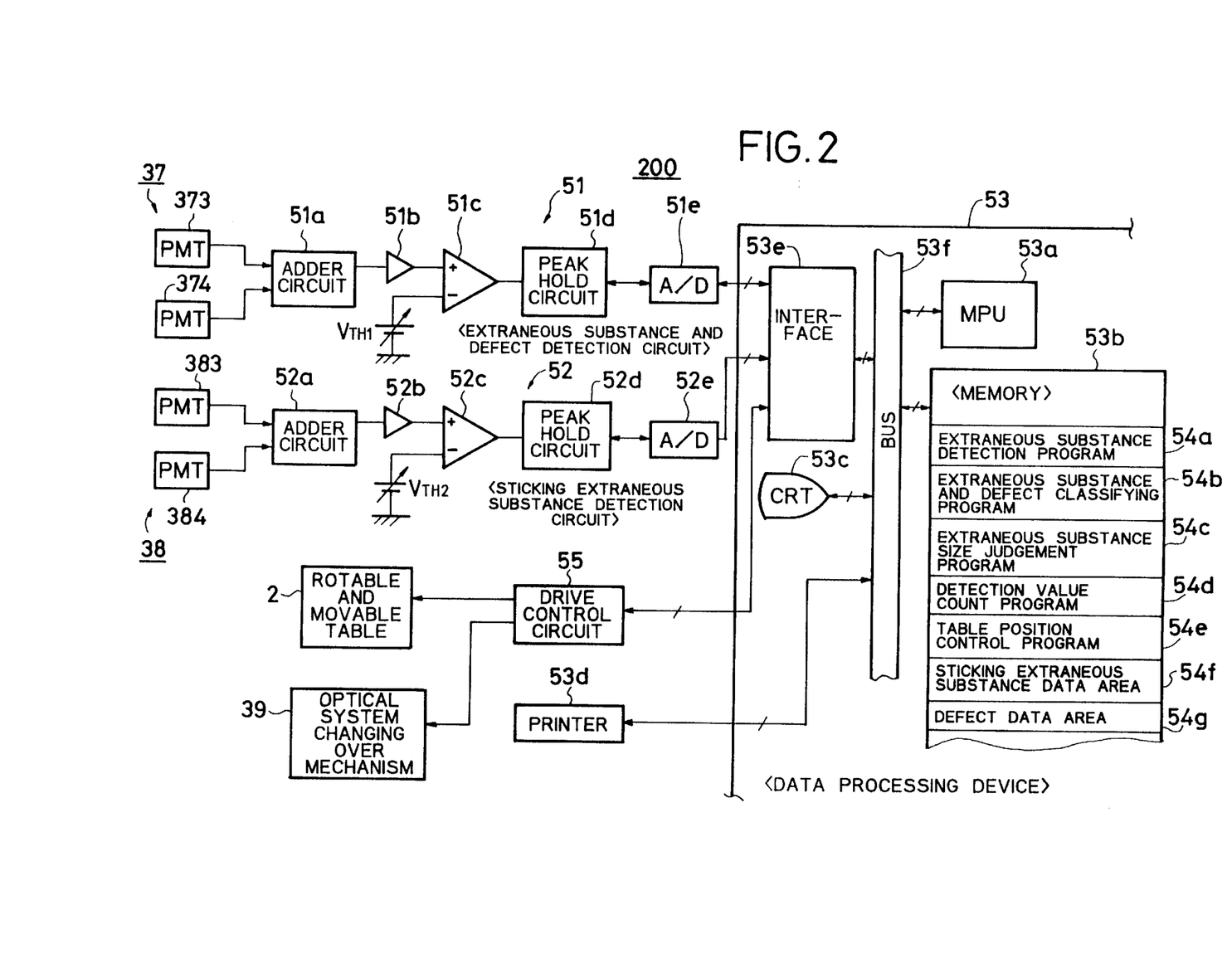
FIG. 2 is a view for explaining the data processing unit in the device.

FIG. 2 shows a constitution of the wafer surface inspection device 200 excluding the optical inspection system 3a.

For the respective high and low light receiving systems an extraneous substance and defect detection circuit 51 and a sticking extraneous substance detection circuit 52 are provided, which correspond to the extraneous substance detection circuit 41 in FIG. 10.

The extraneous substance detection circuit 51 is constituted by an adder circuit 51a which adds the detection signals from the PMTs 373 and 374 in the high angle light receiving system, an amplifier 51b which amplifies the added detection signals and outputs the same, a differential amplifier 51c of one sided amplification which receives the output from the amplifier 51b, compares the same with a predetermined threshold value $V_{TH1}$ and amplifies that portion of the signal exceeding the threshold value, a peak hold circuit 51d and an A/D converter circuit (A/D) 51e. The sticking extraneous substance detection circuit 52 is constituted by an adder circuit 52a which adds the detection signals from the PMTs 383 and 384 in the low angle light receiving system, an amplifier 52b which amplifies the added signals and outputs the same, a differential amplifier 52c of one sided amplification which receives the output from the amplifier 52b, compares the same with a predetermined threshold value $V_{TH2}$ and amplifies that portion of the signal exceeding the threshold value, a peak hold circuit 51d and an A/D converter circuit (A/D) 52e.

The above mentioned threshold values $V_{TH1}$ and $V_{TH2}$ are adjustable, and are respectively set at optimum values depending on the condition of the detection signals of the respective light receiving systems.

As a result, extraneous substance detection signals which are generated by the spiral scanning over the wafer 1 and which contain information relating to sticking extraneous substances, defects and the like, are held at the peak hold circuit 51d, and at the same time the detection signals representing the sticking extraneous substances are held at the peak hold circuit 52d. The respective held values are converted into digital values via the A/Ds 51e and 52e in response to control signals from the data processing device 53, and are fetched into the data processing device 53. The held values in the peak hold circuits 51d and 52d are respectively reset based on signals from the A/Ds 51e and 52e, and the peak values of the subsequent detection signals are respectively held at the peak hold circuits 51d and 52d.

The data processing device 53 is constituted by a microprocessor (MPU) 53a, a memory 53b, a display 53c, a printer 53d, an interface 53e and the like which are interconnected with each other via a bus 53f. Furthers in the memory 53b, an extraneous substance detection program 54a, an extraneous substance and defect classifying program 54b, an extraneous substance size judgement program 54c, a detection value count program 54d, a table position control program 54e and the like are provided, along with, an extraneous substance data area 54f and a defect data area 54g.

Through execution of the table position control program 54e, the MPU 53a controls the rotatable and movable table 2 via the interface 53e and starts the scanning operation, and the control thereby is stored at a predetermined area in the memory 53b as scanning position information.

The extraneous substance detection program 54a causes data to be fetched from the A/Ds 51e and 52e at a predetermined timing via the interface 53e, and to be stored in the memory 53b together with the scanning position data. When the data obtained from the A/Ds 51e and 52e on the detection value data sampled at the same detection position are above the predetermined values respectively set therefor, the extraneous substance and defect classifying program 54b causes the data value to be extracted as detection data of a sticking extraneous substance and to be stored in the extraneous substance data area 54f. When the data obtained from the A/D 52e is below the predetermined value set therefor and the data obtained from the A/D 51e is above the predetermined value set therefor, the extraneous substance and defect classifying program 54b causes the data value to be extracted as detection data of a defect, and to be stored in the defect data area 54g. The reason why the detection data above the predetermined value are used is for eliminating noise data.

According to the extraneous substance size judgement program 54c, the data is read from the extraneous substance data area 54f, to ranked as to size thereof depending on the values thereof, information is added with respect to size (data representing the size thereof) for the respective data, and the data is store the same at the original storage position thereof in the extraneous substance data area 54f.

Further, according to the extraneous substance size judgement program 54c, the data is read from the defect data area 54g, to ranked as to size depending on the values thereof, information is added with respect to size (data representing the size thereof) for the respective data, and the data is stored at the original storage position thereof in the defect data area 54g.

The detection value count program 54d counts the number of sticking extraneous substances for every size with reference to the data in the extraneous substance data area 54f, and calculates the total number of the sticking extraneous substances.

Similarly, the detection value count program 54d counts the number of defects for every size with reference to the data in the defect data area 54g and, calculates the total number of the defects.

The above explained extraneous substance detection program 54a is a program which samples data from a general measuring instrument, the extraneous substance and defect classifying program 54b is a program which only performs classification with reference to data values, and the sticking extraneous substance size judgement program 54c is also a general program which performs ranking with reference to predetermined ranges. Further, the detection value count program 54d is a program which simply counts a predetermined data. As indicated above these programs are not special ones, therefore further detailed explanation thereof is omitted.

Figure 3:
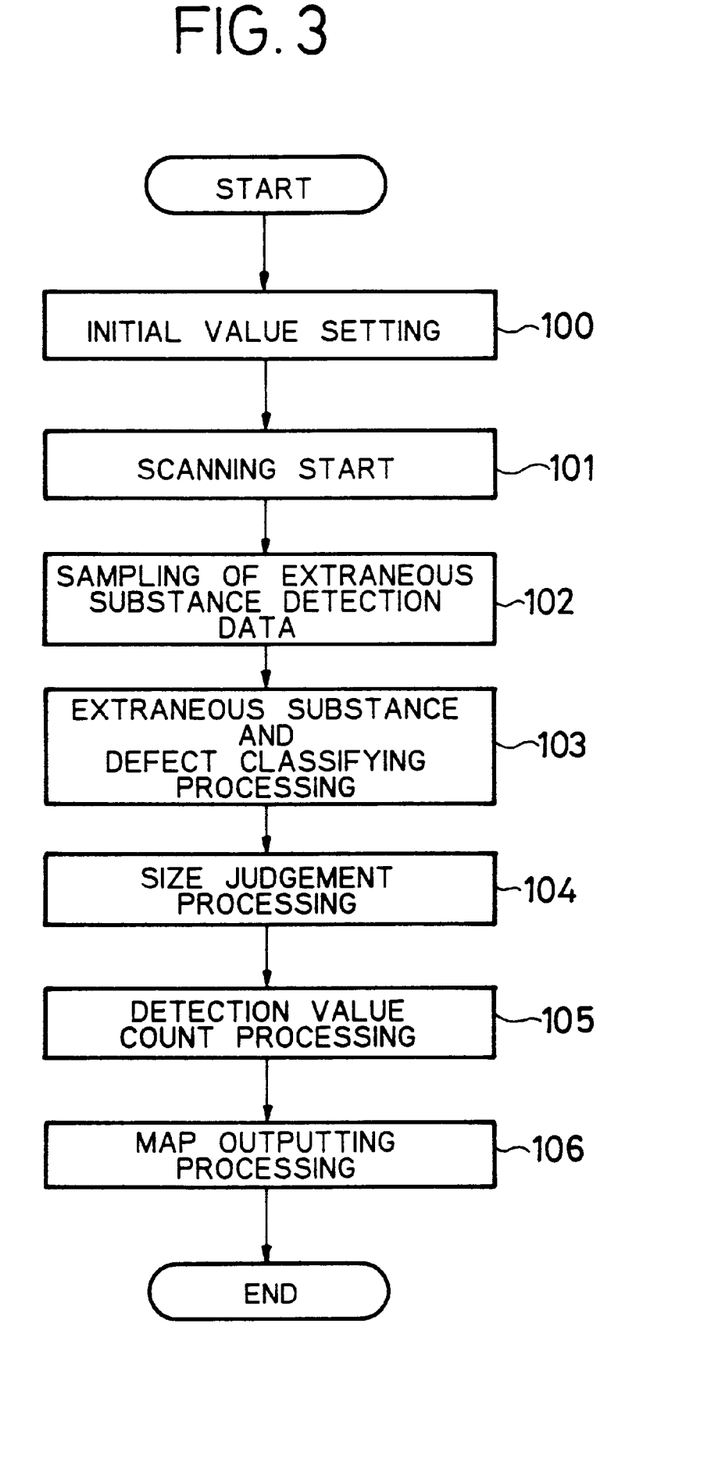
FIG. 3 is a flow chart of detection processing of a sticking extraneous substance and a defect performed in the device.

Now, the detection processing of sticking extraneous substances and defects is explained with reference to FIG. 3. At first, an initial value is set (step 100) and the scanning is started (step 101) Thus, when the spot Sp is projected perpendicularly on the surface of the wafer 1 to start the scanning operation, the scattering light from both the sticking extraneous substances e and the COPs are condensed by the condenser lenses 371 and 372 disposed at right and left sides in the high angle light receiving system 37 and are received by the corresponding PMTs 373 and 374.

On the other hand, into the condenser lenses 381 and 382 in the low angle light receiving system 38, only the scattering light from the sticking extraneous substances e makes incidence and is condensed therein, and is received by the corresponding PMTs 383 and 384.

The received signal of the PMTs 373 and 374 is inputted into the extraneous substance and defect detection circuit 51 wherein the signal is compared with the threshold value $V_{TH1}$ set therefor to remove noise, and signals relating to both sticking extraneous substances e and defects are detected. The respective detected signals are converted into digital values via the A/D 51e and are outputted to the interface 53e. Further, the received signals of the PETs 383 and 384 are inputted into the sticking extraneous substance detection circuit 52 wherein noise is similar removed and only the signal relating to the sticking extraneous substances e is detected, and the detected signals are converted into digital values via the A/D 52e and are outputted to the interface 53e.

The MPU 53a executes the extraneous substance detection program 54a and samples the detection data of the low and high angle light receiving systems from the interface 53e (step 102), and further executes the extraneous substance and defect classifying program 54b to perform the extraneous substance and defect classification (step 103). Subsequently, the MPU 53a executes the extraneous substance size judgement program 54c to judge the size of sticking extraneous substances (step 104) then further executes the detection value count program 54d to count the number of sticking extraneous substances depending on the size thereof and to calculate the total number of the sticking extraneous substances. Further, also for the defects, the program 54c is executed to count the number of the defects depending on the size thereof and to calculate the total number of the defects and the total number of the sticking extraneous substances and defects (step 105). The sticking extraneous substances and the defect are then output separately or together, separated for example, by colors in a map form (step 106). Of course, both can be displayed without a coloring separation. As a result, the extraneous substance maps such as those illustrated in FIG. 7(a) through FIG. 7(d) are obtained.

Figure 4:
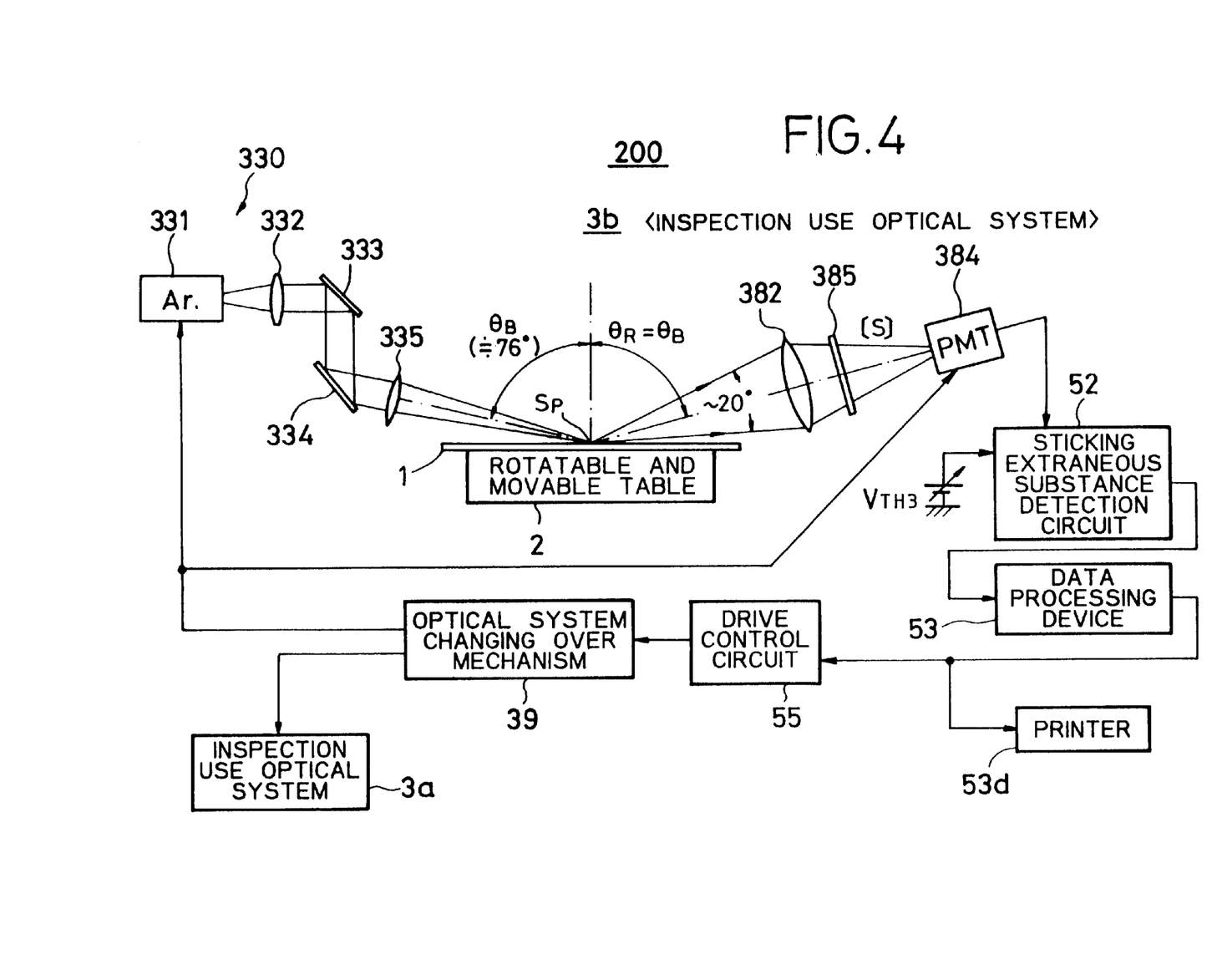
FIG. 4 is a view for explaining an embodiment in which the Brewster angle is further applied for the extraneous substance detection system in the optical system shown in FIG. 1.

In an optical inspection system 3b as illustrated in FIG. 4, a low angle light receiving system 38a is provided in which an S-polarized filter 385 is disposed between the focusing lens 382 and the PMT 384 in a light receiving system which corresponds to the one at the right side of FIG. 1. angle light receiving system as illustrated in FIG. 1, The elevation angle of the optical axis of the light receiving system is set at the Brewster angle of about 14° (depression angle of 76°) with reference to the surface of the wafer 1. The focusing lens 381 and the PMT 383 in a light receiving system which corresponds to the one at the right side of FIG. 1 is eliminated and, in place of the eliminated light receiving system, a light projecting system 330 for irradiating a P-polarized laser spot in included, the light projecting axis of which is set at an elevation angle of about 14° corresponding to the Brewster angle of the wafer. The optical inspection system 3b is changed over from the system 3a via an optical system changing over mechanism 39 and is disposed above the wafer 1. Such changing over is performed by the data processing device 53 via the drive control circuit 55 after completing the inspection by the high angle light receiving system in the optical inspection system 3a. FIG. 4 shows the state after the above explained change over has been completed.

When both the inspection use optical system 3a and the inspection use optical system 3b can be disposed above the wafer 1, it is unnecessary to provide the optical system changing over mechanism 39 and to perform the changing over operation of both optical systems.

The light projecting system 330 in the inspection use optical system 3b is provided with an argon (Ar) laser source 331 for irradiating P-polarized light, and further includes a collimator lens 332, two mirrors 333 and 334, and a focusing lens 335 as indicated in the drawing.

The threshold value of an amplifier in the sticking extraneous substance detection circuit 52 is herein set at $V_{TH3}$ in view of the relationship between the level of detection light and noise.

The constitution of the data processing device 53 is identical to that in the preceeding embodiment. With regard to the processing thereby, in particular the sampling of detection data with the data processing device, at first the extraneous substance and defect detection is performed with the high angle light receiving system 37 through the scanning over the entire surface of the wafer 1, and the detection data thereof are sampled together with the corresponding detection position data. Then after changing over to the inspection optical system 3b, the entire surface of the wafer 1 is again scanned and the detection data sampled at the present time are stored at the same detection position while correlating to the data sampled in the previous detection. The present processing is different on this point from that explained in connection with FIG. 3 wherein the data sampling is performed at once in steps 101 and 102. The processing thereafter is identical to that following the step 103 in the flow chart in FIG. 3.

Figure 5A:
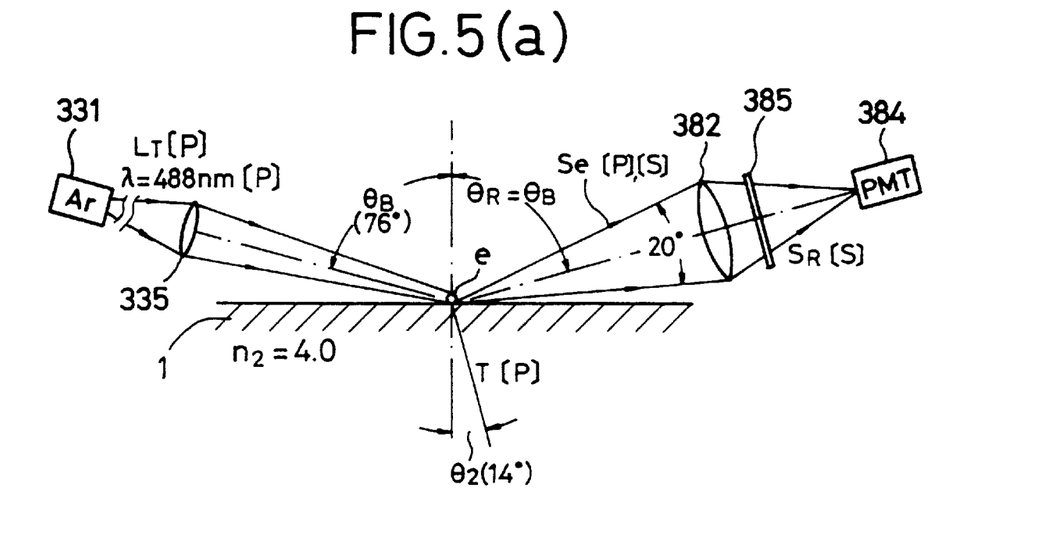
FIG. 5(a), 5(b) and 5(c) are views for explaining scattering light from a sticking extraneous substance and COPs, wherein FIG. 5(a) relates to the sticking extraneous substances FIG. 5(b) relates to COP on the wafer surface, and FIG. 5(c) relates to a COP inside the wafer.
Figures 5B, 5C:
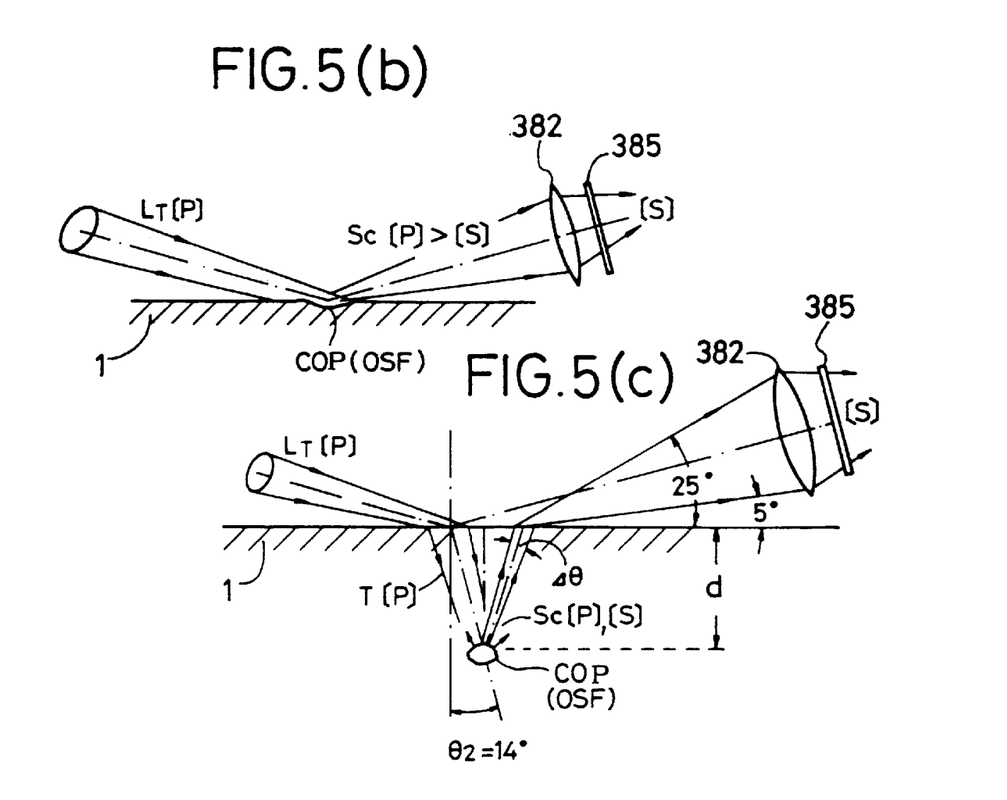

Thereby, as illustrated in FIG. 5(a), the scattering light Se of random polarization from a sticking extraneous substance e on the surface of the wafer 1 is condensed by the condenser lens 382 in the light receiving system 38a and the S-polarized component therein is extracted via the S-polarized filter 385. On the other hand, as illustrated in FIGS. 5(b) and 5(c), COPs and OSFs existing on and inside the wafer 1 scatter the transmitting light T[P], the part of the scattering light Sc of random polarization is condensed by the condenser lens 382 and the S-polarized component is extracted by the S-polarized filter 385. Since the extracted S-polarized component is weak in comparison with the S-polarized component of the scattering light Se from the sticking extraneous substance, the scattering light Se from the sticking extraneous substance e is received by the PMT 383 substantially without reducing the S/N ratio thereof. The extraneous substance detection signal outputted from the PMT 383 is inputted to the sticking extraneous substance detection circuit 52 wherein the detection signal is compared with the threshold value $V_{TH3}$ to remove the noise and sticking extraneous substances e less than 0.1 μm and the respective sizes thereof are detected.

Further, for the sake of convenience of explanation, the output of the PMT 383 is inputted to the sticking extraneous substance detection circuit 52 in the drawing. Principally, the output of the PMT 383 can be inputted to the extraneous substance and defect detection circuit 51 via a change over processing. However, in this instance, the threshold value of the differential amplifier 51c is changed over from $V_{TH1}$ to $V_{TH3}$. If this modification is used, the sticking extraneous substance detection circuit 52 is eliminated.

Figure 6:
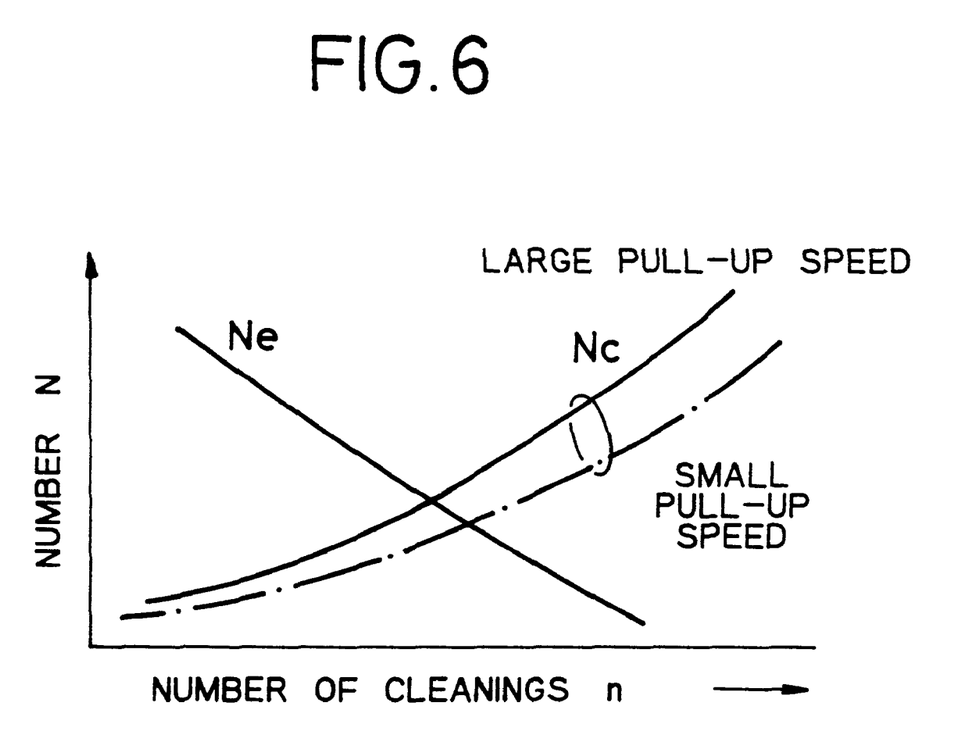
FIG. 6 shows an example of measured data for explaining a correlation between the number of sticking extraneous substances and the number of cleaning.

FIG. 6 shows an example of data representing the number of sticking extraneous substances and COPs measured according to the above explained processing.

In FIG. 6, the abscissa represents number of cleanings n and the ordinate represents number of sticking extraneous substances or COPs. Curves Ne and Nc respectively show the numbers of sticking extraneous substances and COPs larger than 2 μm. The number Ne of the sticking extraneous substances e is naturally decreased in protortion to the number of cleanings. Contrary thereto, the number Nc of the COPs is increased with a substantial increasing rate depending on the number of cleanings. Further, the number Nc is affected by the pulling up speed of the ingot therefor. Manufacturers of wafers can determine an optimum number n of cleanings with reference to these measured data.

The application of the present invention is not limited to blank wafers and it is confirmed, for example, that with the present invention, defects and sticking extraneous substances of a wafer having a deposition film such as aluminum (Al) of thickness of about a few/10 μm can be detected.

Further, the data classification processing between a sticking extraneous substance and a defect in the data processing device can be performed, for example, by setting a flag when scattering light from a certain spot received by the high angle light receiving system is at the same time detected by the low angle light receiving system.

We claim:

1. A wafer surface inspection method, comprising the following steps:

scanning a wafer with laser light, thereby scattering light;

receiving the scattering light;

detecting presence of a wafer abnormality based on the received scattering light; and determining type of wafer abnormality based on the received scattering light;

wherein the detecting step includes a first detecting step and a second detecting step, said first detecting step detecting scattering light only at an elevation angle greater than or equal to 30° with reference to the scanned surface of the wafer, and said second detecting step detecting scattering light only at an elevation angle less than 30°; and wherein the determining step determines that the wafer abnormality is a wafer defect when scattering light is detected at a scanning position in the first detecting step but not at the same scanning position in the second detecting step, and that the wafer abnormality is a sticking extraneous substance when scattering light is detected at the same scanning position in both the first and second detecting steps or at a scanning position in the second detecting step but not at the same scanning position in the first detecting step.

2. A wafer surface inspection method according to claim 1, wherein the scanning step is performed by irradiating a laser beam spot from above the wafer and perpendicular to the wafer surface;

wherein said first detecting step detects scattering light only at an elevation angle between 35°–60°; and wherein said second detecting step detects scattering light only at an elevation angle between 5°–20°.

3. A wafer surface inspection method according to claim 1, wherein signals representing the scattering light received in the first detection step and the scattering light received in the second detection step are respectively sampled depending on the scanning position, and wherein sizes of detected sticking extraneous substances and wafer defects are determined based on the level of the detection signals of the sticking extraneous substances and the level of the detection signals of the wafer defects together with the positional data.

4. A wafer surface inspection method according to claim 1, wherein the determining step determines the type of abnormality based on scattering light received in the receiving step only at elevation angles less than 90°.

5. A wafer surface inspection method according to claim 1, wherein the determining step distinguishes type of wafer abnormality after the detecting step.

6. A wafer surface inspection method, comprising the following steps:

a first scanning step of scanning a wafer with laser light from above the wafer and perpendicular to the wafer surface, thereby scattering light;

a first determining step of determining whether light has scattered at a first elevation angle greater than or equal to 30° with reference to the scanned surface of the wafer as a result of said first scanning step;

if light has scattered at the first elevation angle as a result of said first scanning step, receiving said light scattered at the first elevation angle;

after said first determining step, a second scanning step of scanning the wafer with laser light from above the wafer and oblique to the wafer surface, thereby scattering light;

a second determining step of determining whether light has scattered as a result of said second scanning step at a second elevation angle less than 30°;

if light has scattered at the second elevation angle as a result of said second scanning step, receiving the light scattered at the second elevation angle;

detecting presence of a wafer abnormality when scattering light has been received at at least one of the first and second elevation angles; and a third determining step of determining type of wafer abnormality based on the elevation angle at which scattering light has been received;

wherein the third determining step determines that the detecting step has detected presence of a wafer defect when the scattering light is received only at said first elevation angle; and wherein the third determining step determines that the detecting step has detected presence of a sticking extraneous substance when the scattering light is received only at an elevation angle less than 30°, or at both an elevation angle less than 30° and an elevation angle greater than or equal to 30°.

7. A wafer surface inspection method according to claim 6, wherein the first elevation angle is in a range of 40°–50°;

wherein said second scanning step is performed by irradiating a P-polarized laser beam from an inclined direction having an angle corresponding to the Brewster angle of the wafer;

wherein the second elevation angle is the Brewster angle of the wafer; and wherein said step of receiving the light scattered at the second elevation angle includes the step of S-polarizing the light scattered at the second elevation angle.

8. A wafer surface inspection method according to claim 6, wherein signals representing the scattering light received at the first elevation angle and the scattering light received at the second elevation angle are respectively sampled depending on the scanning position, and wherein the sizes of detected sticking extraneous substances and wafer defects are determined based on the level of the detection signals of the sticking extraneous substances and the level of the detection signals of the wafer defects together with the positional data.

9. A wafer surface inspection method according to claim 6, wherein said first and second elevation angles are both less than 90°.

10. A wafer surface inspection method according to claim 6, wherein the third determining step distinguishes type of wafer abnormality after the detecting step.

11. A wafer surface inspection system, comprising:

a low angle light receiving system including a first photoelectric converter arranged to receive scattering light at an elevation angle less than 30° with reference to the surface of a wafer from which the scattering light is scattered;

a high angle light receiving system including a second photoelectric converter arranged to receive scattering light at an elevation angle equal to or larger than 30° with reference to the surface of a wafer from which the scattering light is scattered;

a scanning mechanism which scans the wafer with a laser beam; and a data processor which receives a first detection signal from said first photoelectric converter and a second detection signal from said second photoelectric converter;

wherein, when the first detection signal is above a first predetermined threshold value but the second detection signal is not above a second predetermined threshold value, or when the first detection signal is above the first predetermined threshold value and the second detection signal is above the second predetermined threshold value, the data processor determines that the wafer has a sticking extraneous substance; and wherein, when the second detection signal is above the second predetermined threshold value but the first detection signal is not above the first predetermined threshold value, the data processor determines that the wafer has a crystal defect.

12. A wafer surface inspection system according to claim 11, further comprising a light projecting optical system which irradiates a spot of the laser beam from above the wafer and perpendicular thereto;

wherein the elevation angle at which said low angle light receiving system receives scattering light is in a range of 5°–20°, and the elevation angle at which the high angle light receiving system receives scattering light is in a range of 35°–60°.

13. A wafer surface inspection system according to claim 11, further comprising a light projecting optical system which irradiates a P-polarized spot of the laser beam from an inclined direction having an angle corresponding to the Brewster angle of the wafer;

wherein the elevation angle at which said low angle light receiving system receives scattering light is selected to be an angle corresponding to the Brewster angle of the wafer, and said low angle light receiving system S-polarizes the scattering light; and wherein the elevation angle at which said high angle light receiving system receives scattering light is in a range of 40°–50°.

14. A wafer surface inspection system according to claim 11, wherein the first and second detection signals are sampled depending on the data of the scanning position, and data of sizes of sticking extraneous substances and crystal defects are produced based on the levels of the first and second detection signals together with the corresponding positional data.

15. A wafer surface inspection system according to claim 11, wherein the first and second photoelectric converters are both set to receive scattering light only at elevation angles less than 90°.

16. A wafer surface inspection system according to claim 11, wherein the data processor distinguishes presence of a sticking extraneous substance from presence of a crystal defect by the first and second detection signals.

* * * * *